United States Patent [19]
Rinner

[11] Patent Number: 5,938,662
[45] Date of Patent: Aug. 17, 1999

[54] HUMAN SPINE FIXATION TEMPLATE AND METHOD OF MAKING SAME

[75] Inventor: James A. Rinner, Racine, Wis.

[73] Assignee: Beere Precision Medical Instruments, Inc., Racine, Wis.

[21] Appl. No.: 09/028,847

[22] Filed: Feb. 24, 1998

[51] Int. Cl.⁶ .................................................... A61B 17/56
[52] U.S. Cl. ................................ 606/60; 606/61; 606/62; 606/63; 606/64; 606/69; 606/73; 606/72; 623/17
[58] Field of Search .................................. 606/60, 61, 62, 606/63, 64, 69, 73, 72; 623/17, 66

[56] References Cited

U.S. PATENT DOCUMENTS

| | | | |
|---|---|---|---|
| 4,409,974 | 10/1983 | Freeland | 128/92 B |
| 4,658,809 | 4/1987 | Ulrich et al. | 606/60 |
| 4,931,055 | 6/1990 | Bumpus et al. | 606/60 |
| 5,562,660 | 10/1996 | Grob | 606/61 |
| 5,658,286 | 8/1997 | Sava | 606/61 |

*Primary Examiner*—Michael Buiz
*Assistant Examiner*—Tan-Uyen T. Ho
*Attorney, Agent, or Firm*—Arthur J. Hansmann

[57] ABSTRACT

A method and template for making a rod to be implanted in a human for affixing the spine of the patient. The template and the method consist of a metal rod covered by a flexible sleeve and end caps.

14 Claims, 2 Drawing Sheets

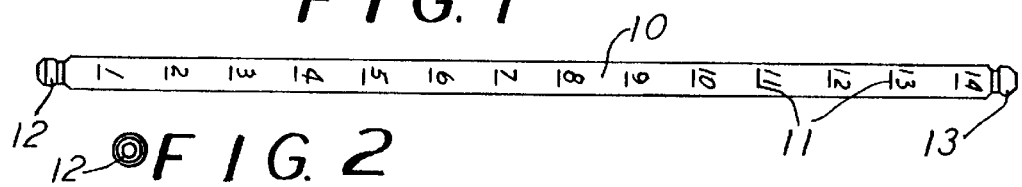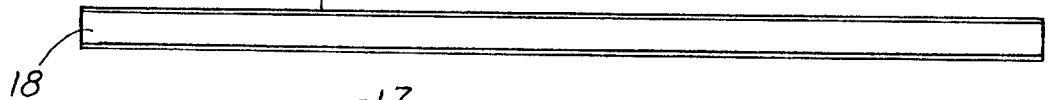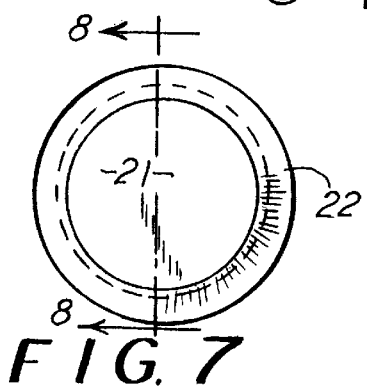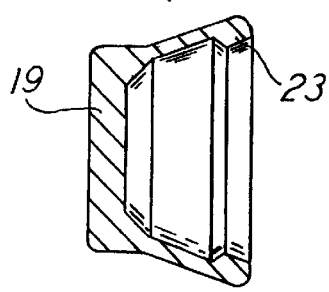

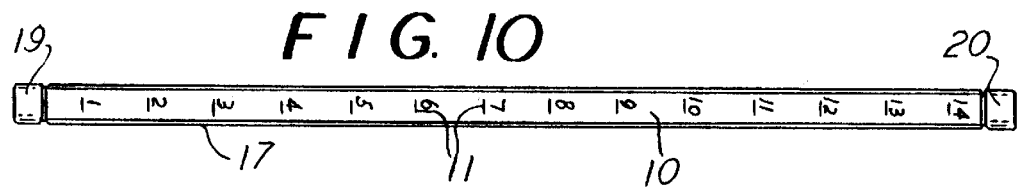
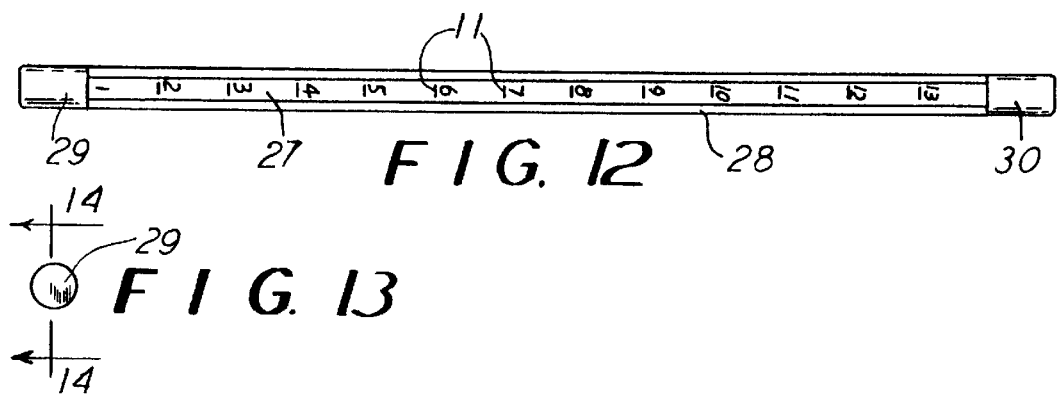
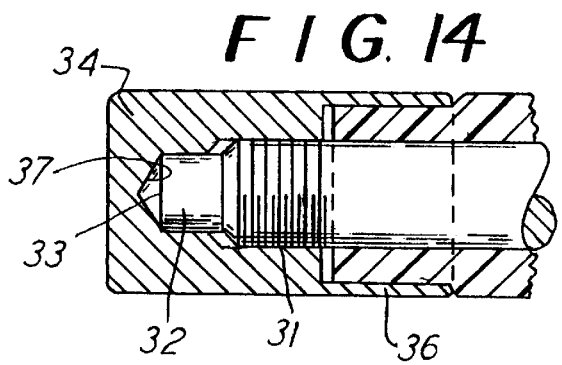

HUMAN SPINE FIXATION TEMPLATE AND METHOD OF MAKING SAME

This invention relates to a human spine fixation template and method of making same.

BACKGROUND OF THE INVENTION

In the medical arts, it is common practice to affix a rod to a patient's spine in order to immobilize the spine in the length adjacent the affixed rod. In that practice, the surgeon determines the necessary length and shape of a rod which is to be implanted in the patient, and that determination is based upon utilizing a template rod which the surgeon initially configures to the shape of the length of the spine which is to be immobilized. That is, the surgeon initially takes a bendable rod and measures and bends the rod to conform to the affected part of the patient's spine. That becomes a template rod which is then utilized for the configuring of a rod which is to be implanted in the patient and secured to that length of the spine.

In that practice, it is important that there be no foreign matter introduced into the patient, and thus the template rod should not deposit any foreign matter in the patient while the surgeon is configuring that template to the patient's spine. However, a rod of a preferred material, such as aluminum, can release foreign particles when it is placed under the forces and action of bending, and of course that is undesirable.

Accordingly, the present invention provides a template rod which does not release foreign matter, that is, its own flakings and the like, when it is being configured or bent adjacent the patient's spine. To accomplish this objective in the present invention, the template rod of this invention is provided with a sleeve which covers the rod and thereby precludes the sloughing or flaking of the rod material. Such sleeve is preferably made of a silicone material which can be snugly positioned over the rod, and two end caps are utilized for fully sealing the assembled rod and sleeve at the ends thereof. As such, the template rod is fully protected and can be bent without leaving any foreign particles in the patient.

The present invention also includes the method of accomplishing the aforementioned and to do so in a manner which provides a protected template rod and does so in an efficient and reasonably cost-effective manner.

Still further, the assembled rod and sleeve of this invention provide for incremental length indicia affixed along the length of the rod so that the surgeon can determine the overall length, as well as the location, for the bends of the template rod. With that information, the surgeon can then use the template to select a final rod and to bend the final rod to conform to the length and configuration of the template rod and then insert the final rod in the patient.

In accomplishing all of the foregoing, the present invention provides the coextensive length of an assembled rod and sleeve with two end caps which extend over the opposite end edges of the sleeve to render the entire assembly of the rod, sleeve, and two end caps fluid and particle passage tight, all so that no fluid or particles can pass to or from the interior of the assembly. In this regard, the present invention swages two end caps over the tubing, all to achieve the aforementioned. Thus the sterility and integrity of the entire assembly is assured. The arrangement is such that the end caps are firmly pressed over the ends of the sleeve or cover extending over the metal rod itself.

BRIEF DESCRIPTION OF THE DRAWINGS

FIG. 1 is a side elevational view of a template rod of this invention.

FIG. 2 is an end elevational view of FIG. 1.

FIG. 3 is an enlarged sectional view of the left end of FIG. 1.

FIG. 4 is a side elevational view of a cover for the rod of FIG. 1.

FIG. 5 is an end elevational view of FIG. 4.

FIG. 6 is an elevational view of a cap used in the template assembly.

FIG. 7 is a left end elevational view of FIG. 6.

FIG. 8 is a sectional view taken on the line 8—8 of FIG. 7.

FIG. 9 is a sectional view of FIG. 3 with the cover of FIG. 4 and the end cap of FIG. 6 assembled.

FIG. 10 is an elevational view of the assembly of the rod, cover, and two end caps.

FIG. 11 is a left end elevational view of FIG. 10.

FIG. 12 is an elevational view of another embodiment of the assembly.

FIG. 13 is a left end elevational view of FIG. 12.

FIG. 14 is an enlarged sectional view of the left end of FIG. 12 and taken along the plane of 14—14 of FIG. 13,

DESCRIPTION OF THE PREFERRED EMBODIMENTS AND THE METHOD

FIGS. 1 and 2 show a template rod 10 which is of a longitudinal and circular configuration in the form of a circular rod. The rod is preferably of an aluminum material which can be bent by a surgeon's finger pressure while the rod is positioned adjacent the patient's spine. As such, the configuration of the rod 10 along its length may have compound bends or several bends therealong to conform to the patient's spine which is to ultimately be immobilized or fixed by another rod which will be made according to the configuration of the template rod 10. As such, the procedure is standard and well-known by those skilled in the art, and the final rod which is to be implanted is not shown herein, but, as mentioned, is well-known to those skilled in the art.

The rod 10 therefore has a longitudinal extent throughout its length, and it has the incremental distance markings for indicia, such as the numbers 1 through 14 as shown in FIG. 10, and this guides the surgeon in establishing the location of the bends for the purpose of finally formulating the final rod which is not shown herein. The rod 10 has the shown indicia designated 11 disposed therealong.

The rod opposite ends 12 and 13 are of a special shape, as best revealed in FIG. 3. Thus, the ends 12 and 13 are of a reduced outer diameter, compared to the diameter of the main extend of the rod 10. Each end 12 and 13 has a circumferential ferential groove 14 and it has a slightly circumferentially larger tip or terminal end 16.

The rod 10 is formed by machining and it is then fully annealed, and it can have a black anodized finish.

FIGS. 4 and 5 show a tubular cover 17 which is made of a clear elastomer such as silicone. The internal diameter at 18 of the sleeve 17 is the measurement of the outer diameter of the rod 10, and the sleeve 17 can be slid over the rod 10 to be snug thereon and to extend for the total length of the rod 10. That is, the rod 10 and the sleeve 17 are coextensive. Also, the sleeve 17 is of transparent material so that the indicia 11 can be seen through the sleeve 17 when the sleeve 17 is on the rod 10, as described.

In a final assembly of the template of this invention, it consists of the rod 10, the sleeve 17, and two end caps 19 and 20, such as that shown in FIGS. 6, 7, and 8. Also, FIG. 10 shows the two caps 19 and 20 in their positions in the final assembly of the template.

The caps 19 and 20 are cup-shaped, and they are cylindrical in general configuration and have an end wall 21 and an integral tapered wall 22, The caps are preferably made of a stainless steel, and the walls 22 can be pressed radially inwardly onto the respective ends 12 and 13 of the rod 10. Thus, as seen in FIG. 9, the final and assembled position for the caps 19 and 20 is with the walls 22 positioned to be of the same outer circumference as the cap end wall 21. In that configuration, the walls 22 are shown to terminate in endless or circular radially inwardly extending flange or tang 23 which aligns with the respective rod groove 14. Therefore, the cap flanges 23 bear radially inwardly on the sleeve 17 to compress the sleeve 17 into the circular groove 14, as seen in FIG. 9.

That is, the end caps 19 and 20 are swaged or compressed radially inwardly from the original configuration such as shown in FIGS. 6, 7, and 8, and thus the caps 19 and 20 are forced down onto the sleeve 17 and cause the sleeve 17 to be pressed into the respective grooves 14. As such, there is a fluid-tight seal over the ends of the rod 10, and thus no material can pass from the rod 10 to the exterior of the template assembly, and thus the required hygeinic and biologically safe template is presented and can be maneuvered adjacent a person's exposed spine.

Of course, with the circular grooves 14 and with the cap tangs 23, there is a firm connection between the caps 19 and 20 and the rod 10 so that the caps 19 and 20 remain fixed with the rod 10 in a secure manner as well as providing the required purity of the entire assembly. As seen in FIG. 9, the relationship is such that in the assembled position shown, the rod grooves 14 and the end walls 24, compared to the overall reach of the cap 19 in the longitudinal direction of the rod 10, is such that the cap surface 26 abuts the rod end wall 24 when the tangs 23 are imbedded toward the grooves 14. In accomplishing that, of course the caps 19 and 20 are of sufficient flexibility so that they can readily be pressed radially inwardly at their circumferential walls 22 without cracking, breaking, or otherwise even distorting, also so that they can achieve the position shown in FIG. 9.

FIG. 10 therefore shows the assembled template with the transparent elastomer 17 extending throughout the length of the interior rod 10, and with the caps 19 and 20 affixed thereto.

FIGS. 12, 13, and 14 show another embodiment of the invention, and here a rod 27 is shown to be encased by its tubular and transparent elastomer cover 28. Again, the rod 27 and the cover 28 are coextensive in their longitudinal extent, and the cover 28 is of the diameter to be snug on the rod 27. End caps 29 and 30 complete the assembly as seen in FIG. 12.

FIG. 12 shows the enlarged end sectional view of FIG. 12, and here it will be seen that the rod 27 has a diametrically reduced end threaded portion 31, and the very terminal end of the rod 27 has a further diametrically reduced end 32, and the rod terminates in an end wall 33.

The cap 29 is again cup-shaped and cylindrical in configuration, and it has its base body portion 34 and it then has its initial tapered portion 36 which is circumferential and comparable to the portion 22 described in connection with the other caps 19 and 20. Thus, in the assembled position shown in FIG. 14, the originally tapered circular wall 36 is compressed radially inwardly to be pressed downwardly onto the elastomer 28, and thus the fluid-tight seal is made at that contact area.

Also, as mentioned, the rod is threaded at 31, and the corresponding interior of the cap 29 is threaded so that the two can be threadedly connected in the position shown in FIG. 14. That is, the cap 29 is initially threaded onto the end of the rod 27 to where the interior cap wall 37 abuts the rod end wall 33, as shown. Therefore, the cap 29 is longitudinally fixed relative to the rod 27. In the final assembly, the cap walls 36 are then radially compressed to seal with the elastomer 28, as shown and as mentioned. In that arrangement, the caps 29 and 30 are threadedly secure with the rod 27, and are further secured therewith by the compression of the tapered walls 36 and form the fluid seal in the final assembly.

Throughout this description, the method is also described and disclosed to one skilled in the art, and it is a part of this invention.

With the template and its bent configuration as formed by the surgeon, the final rod or member can be configured in accord with the incremental measurements displayed along the template, and bending can be by manual or tool assist. Also, the length of one cap 29 and 30 is equal to one increment of measurement as seen in FIG. 12, and thus the very end of say cap 29 starts at zero and extends to the first marking.

In both embodiments, there is a cup-shaped cap which has an endless circular wall and is of a material which can be compressed radially inwardly without damage to the cap.

What is claimed is:

1. A method of making a template for use in implanting a rod into a person's body for skeletal support, comprising the steps of:

forming a template rod of rigid but bendable material and having a length with two terminal ends, forming a sleeve of flexible material and having two terminal ends spaced apart substantially the distance of said length to mate with said terminal ends of said template rod, joining said template rod and said sleeve together to have said sleeve encase and cover said template rod while having said respective terminal ends of said template rod and said sleeve disposed adjacent each other, forming and placing an end cap over each said terminal end of said sleeve to extend radially over said terminal ends, and tightening said end caps radially onto said terminal ends in a manner sufficient to have said end caps completely enclose said terminals ends, all thereby arranged to prevent the passage of any material from said template rod to the exterior of said sleeve and said caps.

2. The method of making a template as claimed in claim 1, including the step of forming said template rod and said sleeve to have substantially the same transverse diameter on the exterior of said template rod and the interior of said sleeve and along the lengths of said template rod and said sleeve, to have said sleeve snug on said template rod.

3. The method of making a template as claimed in claim 2, including the steps of forming said sleeve and said caps to be circular in their exterior surfaces and being of the same external diameter.

4. The method of making a template as claimed in claim 3, wherein said tightening of said caps consists of pressing said caps radially inward onto said sleeve to be in sealed relation therewith.

5. The method of making a template as claimed in claim 1, including the steps of forming said template rod with a circular groove on each of its said terminal ends, and pressing said caps onto said terminal ends and into said grooves for sealing said caps with said sleeve.

6. The method of making a template as claimed in claim 1, including the step of further tightening said caps onto said terminal ends by threading said caps thereon.

7. The method of making a template as claimed in claim 6, including the step of arranging said caps to be of a selected length and threading said caps onto said terminal ends to a selected longitudinal position along said rod.

8. A template for use in making a spine-fixation rod for use in human implant comprising a template rod made of a material which is arranged to be capable of bending in response to force exerted by a user's fingers and which is capable of retaining a bent shape and which has a length and a terminal end at the two extremes of said length, a sleeve made of an elastomer material and being snugly disposed on said template rod and extending for substantially said length of said template rod, and a cap snugly disposed on each said end of said template rod and radially extending over said sleeve and being pressed downwardly thereon and forming an assembly of said template rod and said sleeve and said caps with said assembly being sealed to preclude movement of any said template rod material beyond said assembly.

9. The template for use in making a spine-fixation rod for use in human implant, as claimed in claim 8, wherein said assembly is arranged to be of a cylindrical shape and of a single circumferential size throughout said length of said assembly.

10. The template for use in making a spine-fixation rod for use in human implant, as claimed in claim 8, wherein said template rod has a circular groove at each of said ends thereof, and said caps are cup-shaped and each have a flange extending inwardly thereon and with said flanges being arranged and disposed to fit snugly within said grooves and thereby seal said sleeve with said template rod.

11. The template for use in making a spine-fixation rod for use in human implant, as claimed in claim 8, wherein said sleeve has two ends respectively disposed adjacent ones of said two ends of said template rod, and said caps are disposed to extend radially over said ends of said sleeve and are snug with said sleeve and said template rod.

12. The template for use in making a spine-fixation rod for use in human implant, as claimed in 8, wherein said template rod has length-marking indicia disposed along the length thereof, and said sleeve is of a transparent material and arranged whereby said indicia is visible through said sleeve.

13. The template for use in making a spine-fixation rod for use in human implant, as claimed in claim 8, wherein said template rod and said caps are mutually arranged to have said caps affixed onto said template rod by being threadedly connected thereto and by being radially pressed thereon.

14. The template for use in making a spine-fixation rod for use in human implant, as claimed in claim 8, wherein said assembly consists of only one outer diameter substantially throughout the length of said assembly, said template rod has uniform incremental length-indicia markings therealong, the length of each of said caps along said assembly is the same as one said incremental marking, and said sleeve is transparent so that said indicia on said template rod is visible by viewing through said sleeve.

\* \* \* \* \*